United States Patent
Linares et al.

(10) Patent No.: US 8,932,309 B2
(45) Date of Patent: Jan. 13, 2015

(54) SURGICAL POLYMER MOLDED AND FLEXIBLE COVERING MATERIAL WITH OR WITHOUT SECONDARY COMPOSITE ADDITIVE MATERIALS FOR PROVIDING ANTI-BACTERIAL AND TEAR RESISTANT PROPERTIES

(71) Applicant: Linares Medical Devices, LLC, Auburn Hills, MI (US)

(72) Inventors: Miguel A. Linares, Bloomfield Hills, MI (US); Miguel A. Linares, Jr., Bloomfield Hills, MI (US); Ryan T. Greene, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 45 days.

(21) Appl. No.: 13/787,379

(22) Filed: Mar. 6, 2013

(65) Prior Publication Data

US 2013/0237747 A1    Sep. 12, 2013

Related U.S. Application Data

(60) Provisional application No. 61/607,197, filed on Mar. 6, 2012.

(51) Int. Cl.
| | |
|---|---|
| A61B 17/08 | (2006.01) |
| A61F 2/00 | (2006.01) |
| A61L 27/56 | (2006.01) |
| A61L 27/16 | (2006.01) |

(52) U.S. Cl.
CPC .............. *A61F 2/0063* (2013.01); *A61L 27/56* (2013.01); *A61L 27/16* (2013.01); *A61F 2002/0081* (2013.01); *A61F 2230/005* (2013.01); *A61F 2230/0067* (2013.01)
USPC ......................................... 606/151; 623/23.74

(58) Field of Classification Search
USPC ............. 606/151; 623/23.72–23.76; 424/424, 424/430
See application file for complete search history.

(56) References Cited

U.S. PATENT DOCUMENTS

| | | | |
|---|---|---|---|
| 7,384,550 B2 * | 6/2008 | Rodgers et al. | 210/321.84 |
| 7,530,996 B2 | 5/2009 | Bentele et al. | |
| 7,614,258 B2 * | 11/2009 | Cherok et al. | 66/192 |
| 7,856,984 B2 | 12/2010 | Levernier | |
| 8,177,834 B2 | 5/2012 | Carlson et al. | |
| 2007/0116734 A1 * | 5/2007 | Akash | 424/423 |
| 2009/0192597 A1 | 7/2009 | Bentele et al. | |
| 2011/0082478 A1 | 4/2011 | Glick et al. | |
| 2011/0238094 A1 | 9/2011 | Thomas et al. | |
| 2011/0244170 A1 * | 10/2011 | Hsu et al. | 428/76 |
| 2011/0313450 A1 | 12/2011 | Fortier et al. | |
| 2012/0177904 A1 * | 7/2012 | Gehring, Jr. | 428/220 |
| 2012/0253472 A1 * | 10/2012 | Priewe | 623/23.72 |

* cited by examiner

*Primary Examiner* — Todd Manahan
*Assistant Examiner* — Mikail Mannan
(74) *Attorney, Agent, or Firm* — Gifford, Krass, Sprinkle, Anderson & Citkowski, P.C.

(57) ABSTRACT

A surgically implantable mesh for covering a tear or rupture in a lining associated with an interior body cavity. A mat shaped polymer body has top and bottom spaced apart surfaces which are communicable at intervals by an interior configuration defined in the body and which promotes tissue in-growth following implantation. An antibacterial additive is intermixed with the polymer in a viscous state prior to formation and can included at least one of silver, gold, copper, bronze, or ground bamboo fibers.

4 Claims, 6 Drawing Sheets

SURGICAL POLYMER MOLDED AND FLEXIBLE COVERING MATERIAL WITH OR WITHOUT SECONDARY COMPOSITE ADDITIVE MATERIALS FOR PROVIDING ANTI-BACTERIAL AND TEAR RESISTANT PROPERTIES

CROSS-REFERENCE TO RELATED APPLICATIONS

This Application claims the benefit of U.S. Provisional Application 61/607,197 filed on Mar. 6, 2012, the contents of which are incorporated herein in its entirety.

FIELD OF THE INVENTION

The present application discloses a molded and flexible mesh material, such as constructed of a polymer having a flexible durometer construction and within which is incorporated antibacterial properties. In one non-limiting application, the mesh material can be implanted as a patch or covering over a tear or rupture in various surgical applications as repairs made to the hernia (stomach lining), bowels and other obstetrical/gynecological pelvic repairs. The three dimensional and permeable nature of the flexible mesh material exhibits any of a variety of different undercut patterns, the purpose for which being to encourage in-growth of tissue. Additives to the stock polymeric material formed into the mesh can include, without limitation, any of silver, gold, copper and bronze. Volumes of ground bamboo fibers can also be formed in overlapping fashion and, when integrated within the polymeric base material, provide both strength and flexibility.

BACKGROUND OF THE INVENTION

The prior art is documented with examples of surgical implant fabrics and materials. A first example of this is depicted in each of U.S. Pat. No. 7,530,996 and US 2009/0192597, both to Bentele et al., and which teaches a surgical implant made from a biocompatible fiber material as a woven textile fabric, such as in the form of a vascular prosthesis. The woven fabric is configured so that its permeability to blood is so low that the blood impregnates the textile fabric upon implantation and seals it off by coagulating, but does not flow through it.

Carlson, U.S. Pat. No. 8,177,834, teaches a woven fabric with shape memory element strands woven with textile strands. At least one of the shape memory element strands has at least one float of at least five textile strands between binding points.

Fortier 2011/0313450 teaches a hemostatic patch used to provide hemostasis at the site of anastomosis. The patch includes a body having a substrate, a longitudinal slit bisecting at least a portion of the body, and at least one additional slit extending from the longitudinal slit defining a retractable section.

Thomas, US 2011/0238094 teaches a surgical implant which includes a biocompatible substrate and at least one grip member capable of transitioning between a first non-gripping configuration and a second gripping configuration.

Glick, US 2011/0082478 teaches a suture kit having a plurality of flexible strands of suture, each having one or more suture markings indicative of a suture orientation. A mesh material is configured to enable the strands of suture to be passed therethrough, wherein at least one quadrant or section of the mesh material has one or more mesh markings indicative of a mesh material orientation. The suture and mesh markings include visual indicators, the suture visual indicators corresponding to the mesh visual indicators for indicating a correct orientation of the mesh material with respect to the tissue of a subject.

Finally, Levemier U.S. Pat. No. 7,856,984 teaches a surgical covering material formed by extruding a sheet, either by a blown film or a cast film process. The sheet is constructed of a plurality of layers including an outer exposed textured layer having a surface texture defined by laterally elongated depressions that are oval-like in shape and laterally elongated raised portions. At least one of the other layers is substantially solid and without through openings, and the depressions are the result of the stretching and bursting of bubble formed by the foaming agent as the plurality of layers leave an extrusion die.

SUMMARY OF THE INVENTION

The present invention discloses a surgically implantable mesh for covering a tear or rupture in a lining associated with an interior body cavity. The mesh includes a generally mat shaped polymer body having top and bottom spaced apart surfaces which are communicable at intervals by an interior configuration defined in the body and which promotes tissue in-growth following implantation.

The polymer body further includes a polypropylene or other flexible and durometer rated material. An antibacterial additive is intermixed with the polymer in a viscous state prior to formation and can include at least one of silver, gold, copper, bronze, or ground bamboo fibers.

Other features include the individual pluralities of top and bottom surface closed perimeter apertures being established in spaced apart fashion, with a further plurality of bottom supported projections aligned with the top apertures to establish an undercut profile within the interior configuration of the body. The projections may further incorporate any one of a plurality of spaced apart and elongate extending rails, star shaped projections or modified frusto conical shaped portions.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As will be described in further detail below with reference to the non-limiting examples depicted, the present application discloses a molded and flexible mesh material, such as constructed of a polymer having a flexible durometer construction and within which is incorporated antibacterial properties. In one non-limiting application, the mesh material can be implanted as a patch or covering over a tear or rupture in various surgical applications as repairs made to the hernia (stomach lining), bowels and other obstetrical/gynecological pelvic repairs.

As will also be described below, the three dimensional and permeable nature of the flexible mesh material exhibits any of a variety of different undercut patterns, the purpose for which being to encourage in-growth of tissue. Additives to the stock polymeric material formed into the mesh can include, without limitation, any of silver, gold, copper and bronze. Volumes of ground bamboo fibers can also be formed in overlapping fashion and, when integrated within the polymeric base material, provide both strength and flexibility.

Figure 1:
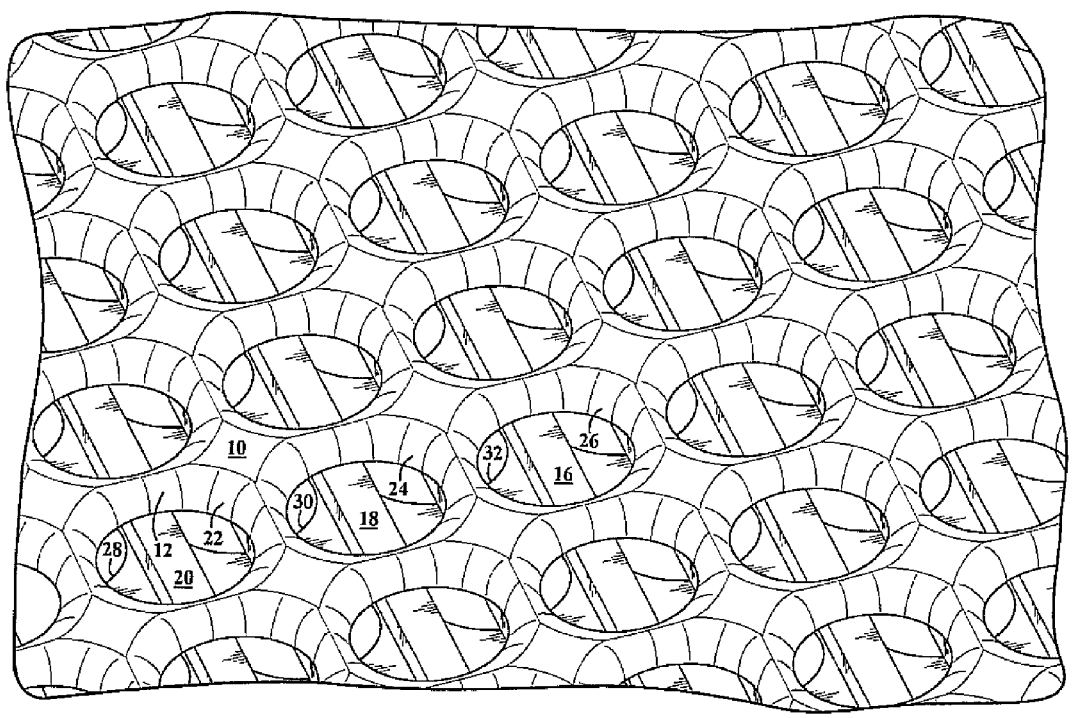
FIGS. 1 and 2 respectively depict are a pair of first and second cutaway perspective views depicting a first three dimensional and permeable implantable mesh configuration exhibiting one desired undercut configuration with interior lengthwise rails for promoting the in-growth of surrounding tissue.
Figure 2:
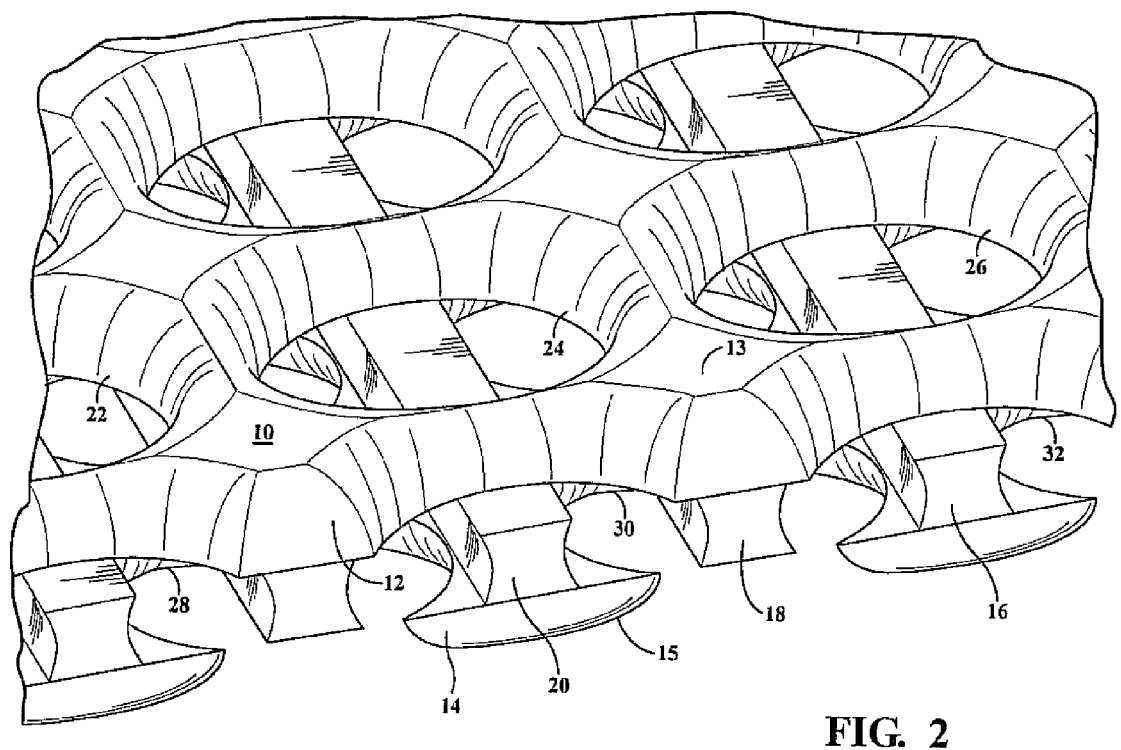

Referring now to FIGS. 1 and 2, a pair of perspective views depict a first three dimensional and permeable implantable mesh configuration 10 which is constructed according to a suitable molding process and so that a base material of an appropriately durometer rated polymer (such as polypropylene) is mixed in an initially viscous or flowable heated state as a composite with any one or more of the additive materials previously recited and again including silver, gold, copper, bronze, or ground bamboo fibers. As better shown in the cutaway perspective of FIG. 2, the formed mesh 10 exhibits a three dimensional profile with an upper layer 12 exhibiting an upper surface 13 and a lower layer 14 exhibiting a lower or bottom surface 15, these separated by a plurality of ribs 16, 18, 20 et seq. which are configured in the shape of elongated space apart rails. In this fashion, a tissue in-growth encouraging and permeable condition is provided to the mesh material in the form of circular apertures (see inner perimeter defining surfaces 22, 24, 26 et seq.,) defined in the upper layer 12 and which communicate with offset circular apertures 28, 30, 32 et seq. defined in the lower layer 14 (again FIG. 2). In this fashion, the elongated and spaced rails 16, 18, 20, et. seq. provide the necessary interconnection and bending support to the upper 12 and lower 14 layers of the mesh in order to provide the necessary physical properties in use.

Figure 3:
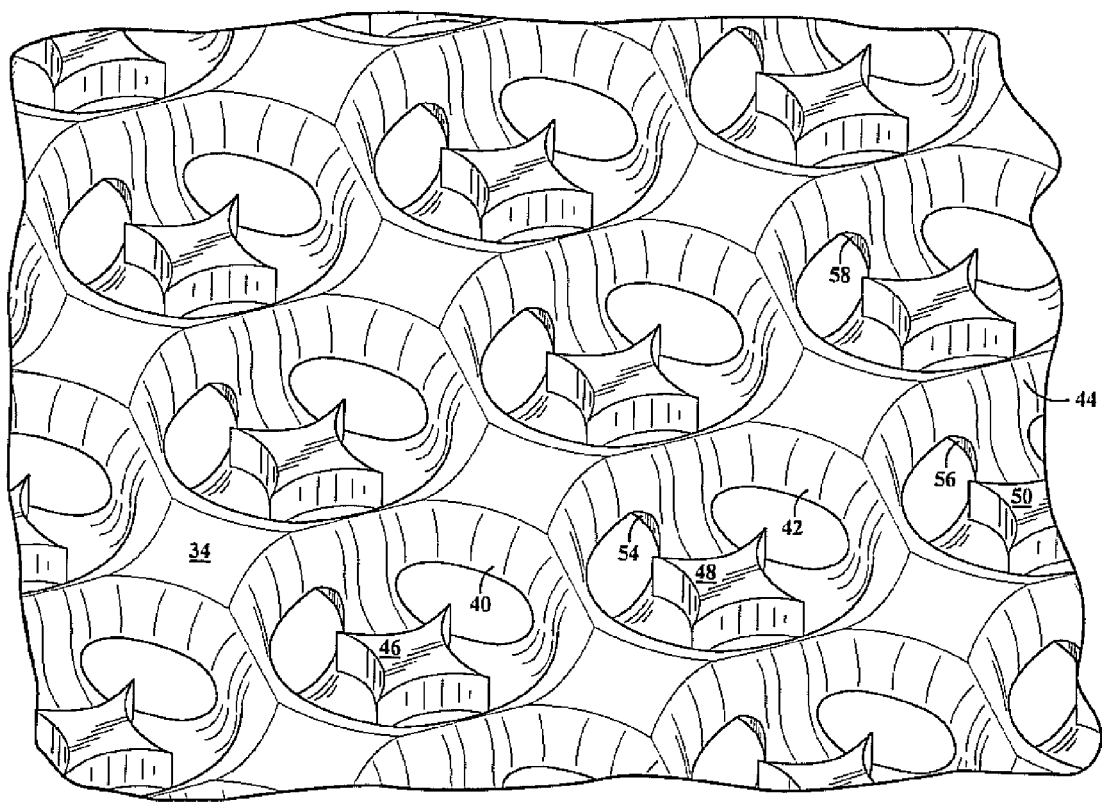
FIGS. 3 and 4 depict a similar pair of first and second cutaway perspective views of a second three dimensional and permeable implantable mesh configuration exhibiting a further undercut configuration with interior positioned star-shaped projections.
Figure 4:
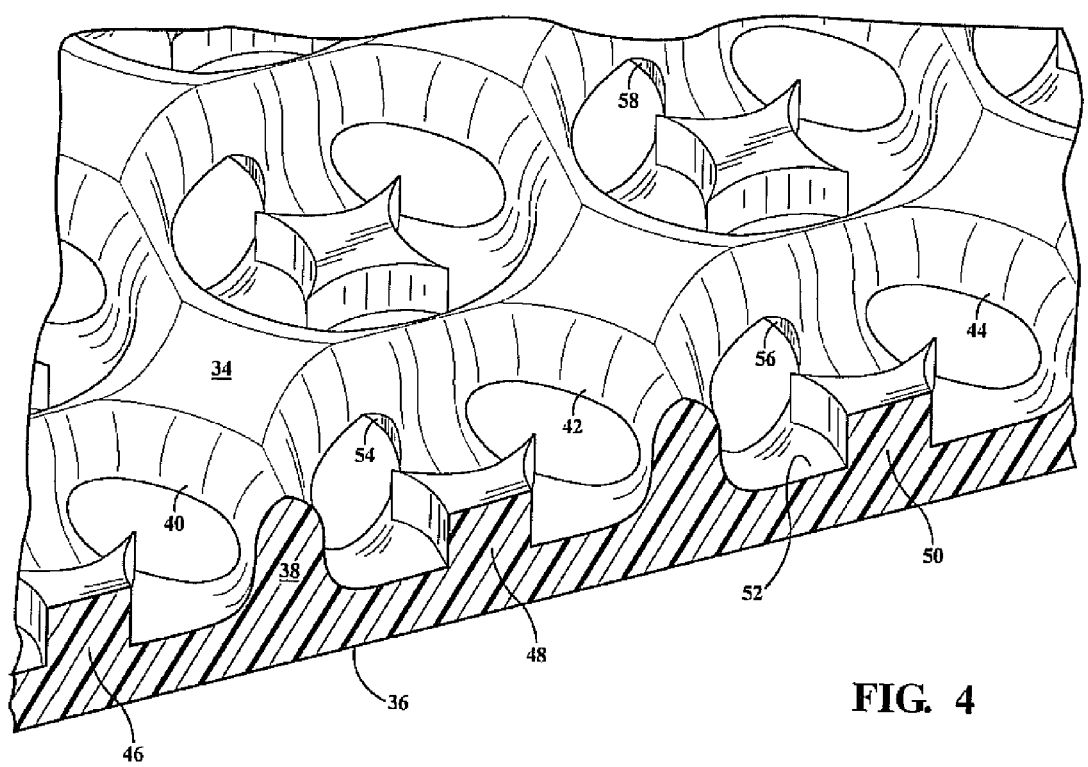

Proceeding to FIGS. 3 and 4, depicted are a similar pair of perspective views of a second three dimensional and permeable implantable mesh configuration, in this instance exhibiting an upper surface 34 and a lower surface 36 separated by spaced circular patterns (see cut away depth profile 38 in FIG. 4) and which further reveal inner perimeter defining surfaces 40, 42, 44 et seq. similar to that previously depicted in FIGS. 1-2. An undercut configuration includes a plurality of interior positioned star-shaped projections, see at 46, 48, 50, et. seq., and which are defined upon an interior or recessed base surface 52 of the mat between the upper 34 and bottom 36 surfaces and, through which are defined a further plurality of bottom situated and likewise offset perimeter defining surfaces 54, 56, 58, et seq., these again similar to those depicted at 28, 30, 32, et seq. in FIG. 2.

Figure 5:
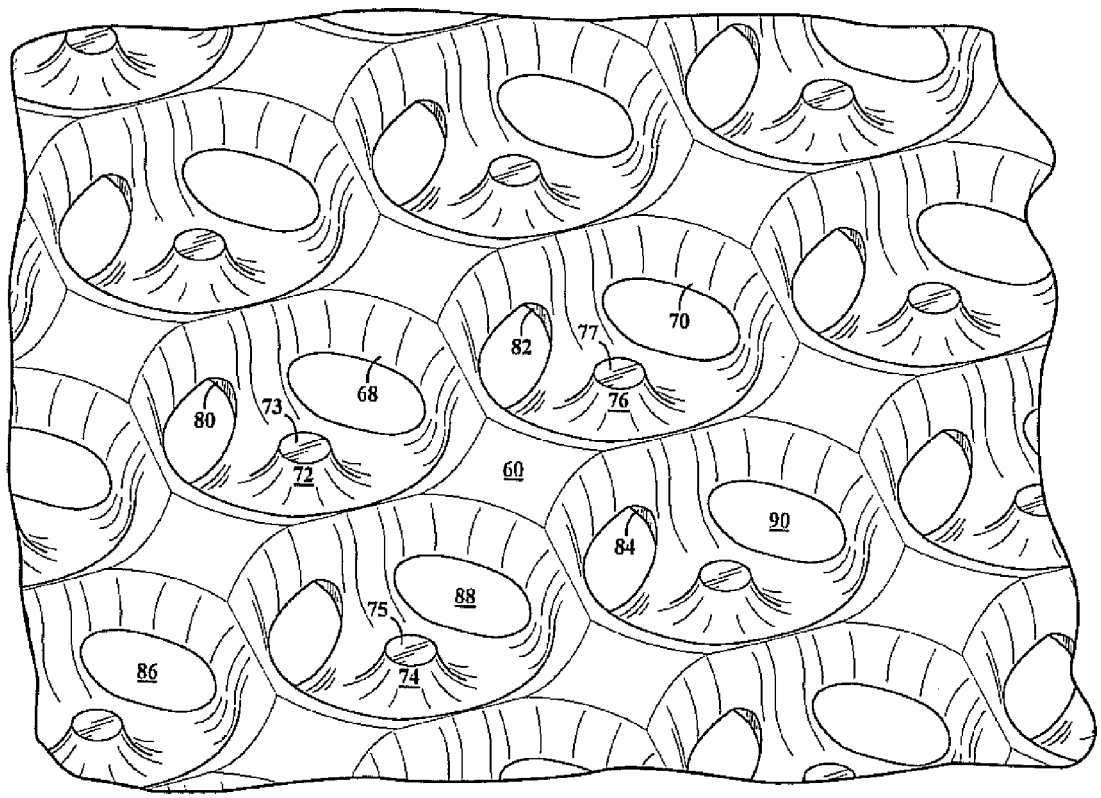
FIGS. 5 and 6 depict a further pair of first and second perspective views of a third mesh implant configuration similar in respects to that shown in FIGS. 3 and 4, with the exception of the star-shaped projections being reconfigured in substantially frusto conical shape with an arcuate curved side which merges into the recessed base surface.
Figure 6:
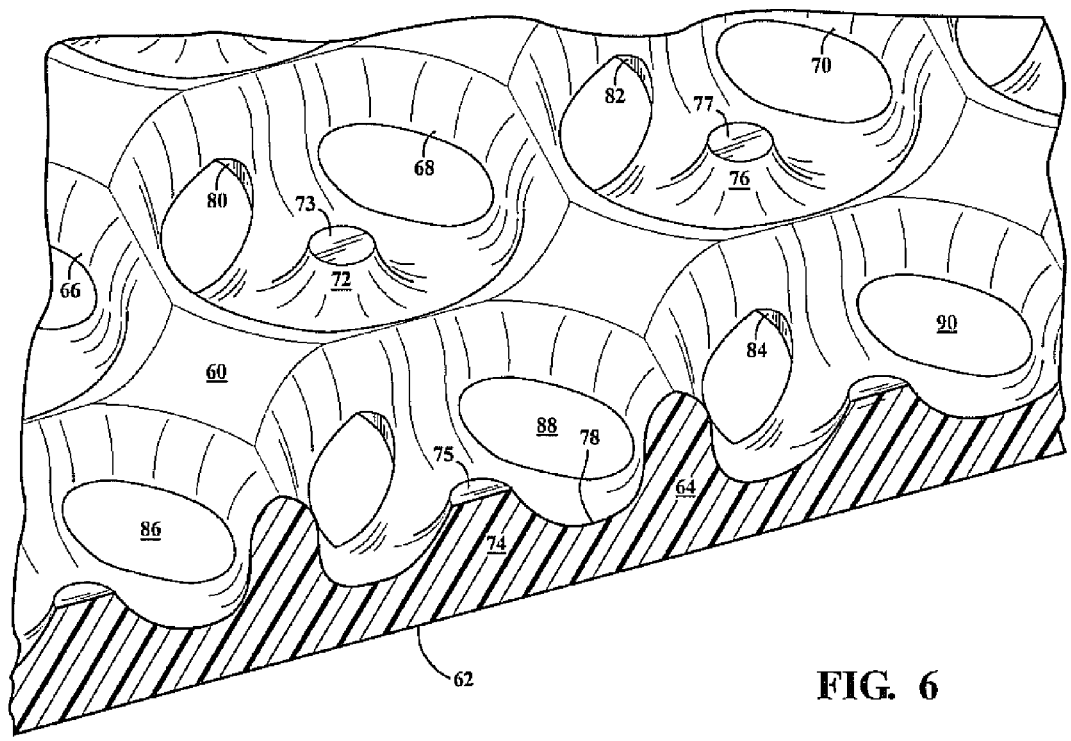

FIGS. 5 and 6 depict a further pair of perspective views of a third mesh implant similar in respects to that shown in FIGS. 3 and 4, and including an upper surface 60 and a lower surface 62 separated by spaced circular patterns (see cut away depth profile 64 in FIG. 6) and which likewise reveals an upper level plurality of spaced apart and inner perimeter defining surfaces 66, 68, 70 et seq. similar to that previously depicted. An undercut configuration includes a plurality of interior positioned and substantially frusto conical shaped portions 72, 74, 76, et seq., each exhibiting a flattened top 73, 75, 77 et. sq., and with an arcuate curved side which merges into a recessed base interior surface 78 located between the upper 60 and lower 62 surfaces, this in turn defining a further plurality of bottom situated and likewise offset perimeter defining surfaces 80, 82, 84, et seq., similar to those depicted in the preceding variants and in order to create permeable and spaced locations (see for example at 86, 88, 90 et seq.) between the upper and lower surfaces of the mesh to facilitate in-growth of tissue following surgical implantation.

The selection of polymeric based material and additive materials (such as in particular the chopped bamboo fibers) can be selected to provide both anti-bacterial and variable flexibility, such accounting for the various demands posed by different surgical applications, e.g. a stomach lining/hernia installation dictating one level of anti-infection and tear resistant requirements, with varying ratings and requirements being applicable to urethral and/or bowel implantations. Cost is another variable such that a mesh implanted with gold is more judiciously employed than one simply embedded with a volume of chopped bamboo fibers. It is also further known that bamboo presents favorable anti-bacterial properties such that its use is merited as an additive to the mesh material.

Having described our invention, other and additional preferred embodiments will become apparent to those skilled in the art to which it pertains, without departing from the scope of the appended claims. This includes the interior communicable nature of the three dimension al mat thickness of the mesh material, along with the possible configuration of the interior projections, being unlimited.

We claim:

1. A surgically implantable mesh for covering a rupture in a lining associated with an interior body cavity, said mesh comprising:
   a generally mat shaped, flexible and polymer based body having an upper layer and a lower layer, each of said layers further including a plurality of closed perimeter defining surfaces which create apertures in said layers;
   said body further including a plurality of elongated and structurally supporting ribs separating said upper and lower layers, said ribs each further including a four sided cross sectional profile;
   a bottom extending side of the four sided profile of each rib extending along a continuous and structurally supporting inner surface of said lower layer separating said lower layer closed perimeter defining surfaces, said upper layer closed perimeter defining surfaces being arranged in both overlapping and partially offsetting fashion relative to said lower layer closed perimeter defining surfaces to promote tissue in-growth following implantation.

2. The mesh as described in claim 1, further comprising an antibacterial additive intermixed with said polymer in a viscous state prior to formation and including at least one of silver, gold, copper, bronze, or ground bamboo fibers.

3. The mesh as described in claim 1, said polymer body further comprising a polypropylene material.

4. The mesh as described in claim 1, further comprising a top extending side of said four sided profile of each rib engaging spaced apart web locations associated with an inner surface of said upper layer, said ribs overlapping each of said upper layer closed perimeter defining surfaces.

* * * * *